(12) United States Patent
Dugan

(10) Patent No.: US 6,441,267 B1
(45) Date of Patent: *Aug. 27, 2002

(54) HEAT BONDABLE BIODEGRADABLE FIBER

(75) Inventor: Jeffrey S. Dugan, Erwin, TN (US)

(73) Assignee: Fiber Innovation Technology, Johnson City, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/286,482

(22) Filed: Apr. 5, 1999

(51) Int. Cl.⁷ .............................. A61F 13/15; D02G 3/02
(52) U.S. Cl. ........................ 604/370; 428/373; 428/370
(58) Field of Search ................................. 604/358, 367, 604/377, 373, 374, 370; 428/373, 374, 370

(56) References Cited

U.S. PATENT DOCUMENTS

| | | |
|---|---|---|
| 3,676,242 A | 7/1972 | Prentice |
| 3,972,759 A | 8/1976 | Buntin |
| 4,041,203 A | 8/1977 | Brock et al. |
| 4,318,949 A * | 3/1982 | Okamoto et al. ............. 428/91 |
| 4,622,259 A | 11/1986 | McAmish et al. |
| 4,710,187 A | 12/1987 | Boland et al. |
| 4,762,521 A | 8/1988 | Roessler et al. |
| 4,766,029 A | 8/1988 | Brock et al. |
| 4,770,656 A | 9/1988 | Proxmire et al. |
| 4,789,592 A | 12/1988 | Taniguchi et al. |
| 4,798,603 A | 1/1989 | Meyer et al. |
| 4,863,785 A | 9/1989 | Berman et al. |
| 5,010,145 A | 4/1991 | Ikada et al. |
| 5,057,368 A | 10/1991 | Largman et al. |
| 5,069,970 A | 12/1991 | Largman et al. |
| 5,082,899 A | 1/1992 | Sawyer et al. |
| 5,108,820 A | 4/1992 | Kaneko et al. |
| 5,142,023 A | 8/1992 | Gruber et al. |
| 5,166,231 A | 11/1992 | Lee et al. |
| 5,167,765 A | 12/1992 | Nielsen et al. |
| 5,171,309 A | 12/1992 | Gallagher et al. |
| 5,277,976 A | 1/1994 | Hogle et al. |
| 5,336,552 A | 8/1994 | Strack et al. |
| 5,382,400 A | 1/1995 | Pike et al. |
| 5,456,982 A | 10/1995 | Hansen et al. |
| 5,506,041 A | 4/1996 | Tanaka et al. |
| 5,593,778 A | 1/1997 | Kondo et al. |
| 5,698,322 A | 12/1997 | Tsai et al. |
| 5,759,569 A | 6/1998 | Hird et al. |
| 5,760,144 A | 6/1998 | Ozeki et al. |
| 5,788,684 A * | 8/1998 | Abuto et al. ................. 604/368 |
| 5,807,973 A | 9/1998 | Gruber et al. |
| 5,814,404 A | 9/1998 | Rutherford et al. |
| 5,916,678 A * | 6/1999 | Jackson et al. ............. 428/370 |
| 5,976,694 A * | 11/1999 | Tsai et al. ................... 428/373 |
| 6,162,537 A * | 12/2000 | Martin et al. ................ 428/373 |

* cited by examiner

*Primary Examiner*—Aaron J. Lewis
*Assistant Examiner*—Jamisue Webb
(74) *Attorney, Agent, or Firm*—Alston & Bird LLP

(57) ABSTRACT

Disclosed are multicomponent fibers wherein at least one component comprises a conventional, non-biodegradable synthetic polymer forming the exposed surface of the multicomponent fiber, thereby permitting thermal bonding of the multicomponent fiber to other fibers. The fibers also include at least one biodegradable component. The multicomponent fibers are useful in the manufacture of nonwoven structures, and in particular nonwoven structures used as a component in disposable absorbent products.

44 Claims, No Drawings

HEAT BONDABLE BIODEGRADABLE FIBER

FIELD OF THE INVENTION

The present invention relates to heat bondable multicomponent fibers, and more particularly heat bondable multicomponent fibers having a biodegradable polymeric component, as well as articles incorporating the fibers as a component thereof

BACKGROUND OF THE INVENTION

Synthetic fibers are widely used in a number of diverse applications to provide stronger, thinner, and lighter weight products. Synthetic fibers are typically heat adhesive (thermobondable) and thus are particularly attractive for the manufacture of nonwoven fabrics, either alone or in combination with other fibers (such as cotton, wool, and wood pulp). Nonwoven fabrics, in turn, are widely used as components of a variety of articles, including without limitation absorbent personal care products, such as diapers, incontinence pads, feminine hygiene products, and the like; medical products, such as surgical drapes, sterile wraps, and the like; filtration devices; interlinings; wipes; furniture and bedding construction; apparel; insulation; and others.

Nonwoven fabrics can be formed entirely of synthetic fibers or a mixture of synthetic and natural fibers (such as cellulosic fibers). For example, typically disposable absorbent products include an absorbent core formed of cellulosic fluff pulp. The absorbent core can also include thermobondable synthetic fibers to thermally bind the cellulose fibers together, thereby achieving an absorbent material with improved strength. The product can also be thinner and lighter weight than traditional products.

Conventional synthetic fibers, however, do not naturally degrade, thus creating problems associated with the disposal of products containing such fibers. In particular, recycling articles containing a blend of natural and conventional synthetic fibers is generally not cost effective, yet the disposal of these articles in landfills generates significant amounts of non-degradable waste. As landfills reach their capacity, the demand has increased for the incorporation of more degradable components in disposable products, as well as the design of products that can be disposed of by means other than by incorporation into solid waste disposal facilities.

To address concern over the issue of solid waste disposal, biodegradable polymers are increasingly used as a replacement for conventional synthetic polymers. Biodegradable polymers of interest include water-soluble polymers such as polyvinyl alcohol; naturally synthesized polymers such as sodium alginate and microbial polyesters; hydrolyzable aliphatic polyester and polyurethane polymers; and the like. Synthetic biodegradable aliphatic polyesters include polyglycolide and poly(lactic)acid polymers. See, for example, U.S. Pat. Nos. 5,166,231; 5,506,041; 5,759,569; and 5,171,309.

Of particular interest is the use of lactic acid to manufacture biodegradable resin. Poly(lactic) acid (hereinafter"PLA") was initially introduced as a biodegradable polymer for medical products. U.S. Pat. Nos. 5,142,023 and 5,807,973 to Gruber et al. disclose processes by which a nonmedical grade of poly(lactic) acid may be produced and utilized in nonwoven fabrics. Examples of biodegradable fibers comprised entirely of polylactic acid polymers and/or copolymers are found in U.S. Pat. Nos. 5,010,145 and 5,760,144. See also U.S. Pat. Nos. 5,698,322 and 5,593,778 (directed bicomponent fibers which include poly(lactic acid) components).

The successful inclusion of biodegradable materials in disposable absorbent products provides several avenues by which these products may be discarded once their useful life has ended. Primarily, these articles may be easily and efficiently disposed of by composting. Alternatively, the disposable absorbent product may be easily and efficiently disposed of to a liquid sewage system wherein the disposable absorbent product is capable of being degraded.

Although biodegradable fibers are known, problems have been encountered with their use, for example, lack of control of the onset of polymer degradation. It is essential that the biodegradable fiber maintain its integrity until its useful life has ended. U.S. Pat. No. 5,593,778 is directed to a core/sheath bicomponent fiber comprised entirely of poly(lactic acid), wherein the core PLA component biodegrades at a faster rate than the sheath. Although such fibers can provide some benefits, such fibers merely delay the onset of degradation and do not provide means for proactively controlling or initiating degradation of biodegradable fibers.

SUMMARY OF THE INVENTION

The present invention provides multicomponent heat adhesive or thermobondable fibers which exhibit a number of desirable, yet contradictory, properties in a single fiber structure. The fibers of the invention include a biodegradable polymeric component, thereby providing advantages in the disposal of products made with such fibers. However, in contrast to prior biodegradable fiber constructions, the fibers of the invention are structured so that initiation of degradation can be readily controlled.

In this regard, in addition to a biodegradable component, the fibers of the invention also include a thermobondable non-biodegradable polymeric component. The non-biodegradable polymeric component forms the exposed outer surface of the fibers, completely encapsulating the biodegradable component. To control fiber degradation, the non-biodegradable polymer and biodegradable polymer can be selected so that the non-biodegradable polymer has a lower melting point (preferably at least about 10° C. lower) than the melting point of the biodegradable polymer. The fibers can accordingly be thermally treated to melt away at least a portion of the non-biodegradable polymer component to expose the biodegradable component to conditions necessary to initiate decomposition or degradation thereof. Thus the fiber degradation process can be proactively initiated, rather than merely slowed or delayed, by protecting the biodegradable component from the environment until such a time as its degradation is purposefully triggered.

The present invention also provides fabrics formed of the multicomponent fibers of the invention, articles incorporating such fabrics as a component, processes for making the fibers and processes for controlling the degradation of articles made using the fibers.

DETAILED DESCRIPTION OF THE INVENTION

The present invention will be described more fully hereinafter in connection with illustrative embodiments of the invention which are given so that the present disclosure will be thorough and complete and will fully convey the scope of the invention to those skilled in the art. However, it is to be understood that this invention may be embodied in many different forms and should not be construed as being limited to the specific embodiments described and illustrated herein. Although specific terms are used in the following description, these terms are merely for purposes of illustration and are not intended to define or limit the scope of the invention.

The multicomponent fibers of the invention include at least two structured polymeric components, a thermobondable non-biodegradable synthetic polymeric component and a biodegradable polymeric component. Multicomponent fibers are formed of two or more polymeric materials. For purposes of illustration only, the present invention will generally be described in terms of a bicomponent fiber comprising two components. However, it should be understood that the scope of the present invention is meant to include fibers with two or more components.

In general, the components are arranged in substantially constantly positioned distinct zones across the cross section of the multicomponent fiber and extend continuously along the length of the multicomponent fiber. A preferred configuration is a sheath/core arrangement, wherein a first component, the sheath, substantially surrounds a second component, the core. However, other structured fiber configurations as known in the art may potentially be used, such as but not limited to, "islands-in-the-sea" arrangements, and the like. Reference is made to U.S. Pat. No. 5,108,820 to Kaneko et al., U.S. Pat. No. 5,336,552 to Strack et al., and U.S. Pat. No. 5,382,400 to Pike et al. for a further discussion of multicomponent fiber constructions. The multicomponent fibers may also have unconventional shapes (such as multilobal) such as described in U.S. Pat. No. 5,277,976 to Hogle et al., and U.S. Pat. Nos. 5,057,368 and 5,069,970 to Largman et al.

The cross section of the multicomponent fiber is preferably circular, since the equipment typically used in the production of multicomponent synthetic fibers normally produces fibers with a substantially circular cross section. The configuration of the first and second components in a fiber of circular cross section can be either concentric or acentric, the latter configuration sometimes being known as a "modified side-by-side" or an "eccentric" multicomponent fiber.

The concentric configuration is characterized by the first component having a substantially uniform thickness, such that the second component lies approximately in the center of the fiber. In the acentric configuration, the thickness of the first component varies, and the second component therefore does not lie in the center of the fiber. In either case, the second component is substantially surrounded by the first component. Both the cross section of the fiber and the configuration of the components will depend upon the equipment which is used in the preparation of the fiber, the process conditions and the melt viscosities of the two components.

The thermobondable (or heat adhesive) non-biodegradable polymeric component and the biodegradable polymeric component of the fibers are selected so that the non-biodegradable component has a lower melting or softening temperature than the biodegradable component. Preferably the thermobondable non-biodegradable polymeric has a melting or softening point of at least 10° C., more preferably at least about 20° C., and most preferably at least about 25° C., less than the melting point of the biodegradable polymeric component.

Because the non-biodegradable component has a lower melting point relative to the melting point of the biodegradable polymeric component, the non-biodegradable polymeric component can act as a latent adhesive in thermal bonding processes. Thermal bonding is a well-known method of nonwoven fabric formation in which synthetic fibers are heated to their glass transition point or beyond, causing the fibers to soften and adhere to adjoining fibers, thereby forming a nonwoven fabric. Thus, when the multicomponent fiber is subjected to an appropriate temperature, typically greater than the melting temperature of the first non-biodegradable component but less than the melting temperature of the second biodegradable component, the first component will soften or melt while the second component will generally maintain its rigid form. Thermal bonding conditions will vary depending upon factors such as polymers used, pressure, line speed and the like and can be readily determined by one of skill in the art.

Polymers suitable for use in the first component include polyolefins, polystyrenes, polyurethanes, acetal resins, polyethylene vinyl alcohol, and copolymers, terpolymers, and mixtures thereof. Polyester copolymers and polyamide copolymers are also acceptable for use in the first component. Olefinic resins, long-chain, synthetic polymers of at least 85 weight percent ethylene, propylene or other olefin unit, are of particular interest. Suitable polyolefins include polypropylene, polyethylene, polybutene, and copolymers and mixtures thereof. Specific examples of polyolefins suitable for use in the thermobondable non-biodegradable component include high density polyethylene, linear low density polyethylene, poly(1-butene), polypropylene, and copolymers, terpolymers, and mixtures thereof. In addition, the thermobondable non-biodegradable polymeric component may include mixtures of polyolefins with other polymers, such as but not limited to (ethyl vinyl acetate) copolymers, (ethylene acrylic acid) copolymers, and the like. In a preferred aspect of the invention, polyethylene is employed, in particular, high density polyethylene.

The second component of the fibers of the invention includes a biodegradable polymer as known in the art. As used herein, "biodegradable" refers to a material that degrades under aerobic and/or anaerobic conditions in the presence of bacteria, fungi, algae, and other microorganisms to carbon dioxide/methane, water and biomass, although materials containing heteroatoms can also yield other products such as ammonia or sulfur dioxide. "Biomass" generally refers to the portion of the metabolized materials incorporated into the cellular structure of the organisms present or converted to humus fractions indistinguishable from material of biological origin. As a result, the biodegradable fiber, either in its initial form or after incorporation into a fabric, will begin to degrade when exposed to such microorganisms, even if such exposure occurs prior to the expiration of the fiber's useful life. Exemplary biodegradable polymers include, without limitation, polyvinyl alcohol, hydrolyzable aliphatic polyesters, hydrolyzable aliphatic polyurethanes, cis-polyisoprene, cis-polybutadiene, poly (caprolactone), hydrolyzable poly(lactic acid), poly (hydroxy alkanoates), and the like and copolymers and blends thereof. The skilled artisan will appreciate that when poly(lactic acid) is used, the poly(lactic acid) polymer is first hydrolyzed before microorganisms can consume the hydrolysis products.

The biodegradable polymeric component can also be selected to provide strength or rigidity to the fiber and, thus, to nonwoven structures comprising the multicomponent fiber. Strength or rigidity of the fiber is generally achieved by selecting a biodegradable component having a thermal melting temperature greater than the thermal melting temperature of the thermobondable non-biodegradable component. Thus, as noted above, when the multicomponent fiber is subjected to an appropriate temperature, typically greater than the melting temperature of the first non-biodegradable component but less than the melting temperature of the second biodegradable component, the first component will soften or melt while the second component will generally maintain its rigid form.

Preferably the biodegradable polymeric component comprises poly(lactic acid). In addition to biodegradability, poly(lactic acid) can impart other desirable properties to the fibers of the invention. For example, the fibers of the invention which include poly(lactic acid) as a component can exhibit improved tensile strength, as compared to fibers including polyethylene terephthalate or a polyamides as a high temperature core.

Poly(lactic acid) polymer is a biodegradable polyester polymer generally prepared by the polymerization of lactic acid. However, it will be recognized by one skilled in the art that a chemically equivalent material may also be prepared by the polymerization of lactide. Therefore, as used herein, the term "poly(lactic acid) polymer" is intended to represent the polymer that is prepared by either the polymerization of lactic acid or lactide. Reference is made to U.S. Pat. Nos. 5,698,322; 5,142,023; 5,760,144; 5,593,778; 5,807,973; and 5,010,145, the entire disclosure of each of which is hereby incorporated by reference.

Lactic acid and lactide are known to be an asymmetrical molecules, having two optical isomers referred to, respectively as the levorotatory (hereinafter referred to as "L") enantiomer and the dextrorotatory (hereinafter referred to as "D") enantiomer. As a result, by polymerizing a particular enantiomer or by using a mixture of the two enantiomers, it is possible to prepare polymers that are chemically similar yet which have widely differing properties. In particular, it has been found that by modifying the stereochemistry of a poly(lactic acid) polymer, it is possible to control the melting temperature of the polymer.

The degree of crystallinity of a PLA polymer is based on the regularity of the polymer backbone and its ability to line up with similarly shaped sections of itself or other chains. If even a relatively small amount of D-enantiomer (of either lactic acid or lactide), such as about 3 to about 4 weight percent, is copolymerized with L-enantiomer (of either lactic acid or lactide), the polymer backbone generally becomes irregularly shaped enough that it cannot line up and orient itself with other backbone segments of pure L-enantiomer polymer, thus reducing the crystallinity of the polymer, which in turn suppresses the melting point. Based on the foregoing, although a minimal amount of D-enantiomer can be tolerated, preferably the amount of D-enantiomer present in the instant invention is not such that it suppresses the melting point of the PLA component to the melting point of the first component, or to within 10° C. thereof.

Advantageously the PLA polymer also exhibits residual monomer percents effective for the second component to exhibit desirable melt strength, fiber mechanical strength, and fiber spinning properties. As used herein, "residual monomer percent" refers to the amount of lactic acid or lactide monomer that is unreacted yet which remains entrapped within the structure of the entangled PLA polymer chain. In general, if the residual monomer percent of a PLA polymer in a component is too high, the component may be difficult to process due to inconsistent processing properties caused by a large amount of monomer vapor being released during processing that cause variations in extrusion pressures. However, a minor amount of residual monomer in a PLA polymer in a component may be beneficial due to such residual monomer functioning as a plasticizer during a spinning process. Thus, the PLA polymer in the second component generally exhibits a residual monomer percent that is less than about 15 percent, preferably less than about 10 percent, and more preferably less than about 7 percent.

Each of the thermobondable non-biodegradable polymeric component and the biodegradable polymeric component can optionally include other components not adversely effecting the desired properties thereof. Exemplary materials which could be used as additional components would include, without limitation, pigments, antioxidants, stabilizers, surfactants, waxes, flow promoters, solid solvents, particulates, and other materials added to enhance processability of the first and the second components. For example, a stabilizing agent may be added to the biodegradable polymer to reduce thermal degradation which might otherwise occur during the poly(lactic) acid spinning process. The use of such stabilizing agents is disclosed in U.S. Pat. No. 5,807,973, hereby incorporated by reference. Further, additives which enhance the biodegradability of the poly(lactic) acid may optionally be included, as disclosed in U.S. Pat. No. 5,760,144, previously incorporated by reference. These and other additives can be used in conventional amounts.

The weight ratio of the thermobondable non-biodegradable polymeric component and the biodegradable polymeric component can vary. Preferably the weight ratio is in the range of about 10:90 to 90:10, more preferably from about 30:70 to about 70:30, and most preferably from about 40:60 to about 60:40.

As discussed above, the thermobondable non-biodegradable component generally provides the entire exposed surface on the multicomponent fiber, thereby permitting thermal bonding of the multicomponent fiber to other fibers (which may be the same or different from the multicomponent fiber of the present invention). In one preferred aspect of the invention, the thermobondable non-biodegradable polymeric component is the sheath of a sheath/core fiber. As a result, the multicomponent fiber is useful in the production of a wide variety of thermally bonded fibrous nonwoven structures, such as but not limited to carded webs, wet laid webs, dry laid webs, spunbonded webs, meltblown webs, and the like. While particularly useful in the production of nonwoven fabrics, the fibers of the invention can also be used to make other textile structures such as but not limited to woven and knit fabrics.

In addition, the onset of biodegradation in a multicomponent article containing a biodegradable polymer may be delayed until purposefully triggered, thereby extending the anticipated useful life of articles containing such biodegradable polymers. Therefore, in one aspect of the invention, fabric bonding occurs by simply softening the latent adhesive polymer without fully melting it, thereby leaving the latent adhesive polymer layer intact to protect the biodegradable polymer from the environment. Degradation of the fiber or article can then be initiated by a heat treatment of the fiber of the present invention, or article containing such fiber, prior to its disposal in the environment. This heat treatment is effected by exposing the fiber to sufficient energy to decrease the melt viscosity of the latent adhesive polymer so that it flows off of, or melts away from, the surface of the biodegradable polymer, thereby exposing the biodegradable polymer to the environment and triggering subsequent degradation.

The thermobondable non-biodegradable component comprises 100 percent of the surface of the fiber, thereby providing both thermal bonding properties and maximum protection to the biodegradable core. A core/sheath structure is preferred, as noted above. The core/sheath fiber can advantageously be incorporated into a thermally bonded nonwoven fabric, which can then be subjected to a heat treatment after the useful life of the fabric has ended.

In another aspect of this invention, the biodegradable polymer may be exposed to the environment during fabric formation. In this aspect, sufficient energy is supplied during the thermal bonding process to allow the latent adhesive polymer to flow off of the surface of the biodegradable polymer.

Methods for making multicomponent fibers are well known and need not be described here in detail. Generally, to form a multicomponent fiber, at least two polymers are extruded separately and fed into a polymer distribution system wherein the polymers are introduced into a segmented spinneret plate. The polymers follow separate paths to the fiber spinneret and are combined in a spinneret hole. The spinneret is configured so that the extrudant has the desired shape.

Following extrusion through the die, the resulting thin fluid strands, or filaments, remain in the molten state for some distance before they are solidified by cooling in a surrounding fluid medium, which may be chilled air blown through the strands. Once solidified, the filaments are taken up on a godet or another take-up surface. In a continuous filament process, the strands are taken up on a godet which draws down the thin fluid streams in proportion to the speed of the take-up godet. In the jet process, the strands are collected in a jet, such as for example, an air gun, and blown onto a take-up surface such as a roller or a moving belt to form a spunbond web. In the meltblown process, air is ejected at the surface of the spinnerette which serves to simultaneously draw down and cool the thin fluid streams as they are deposited on a take-up surface in the path of cooling air, thereby forming a fiber web. Regardless of the type of melt spinning procedure which is used, it is important that the thin fluid streams be melt drawn down in a molten state, i.e. before solidification occurs to orient the polymer molecules for good tenacity. Typical melt draw down ratios known in the art may be-utilized. Where a continuous filament or staple process is employed, it may be desirable to draw the strands in the solid state with conventional drawing equipment, such as, for example, sequential godets operating at differential speeds. See, for example, U.S. Pat. No. 5,082,899.

Following drawing in the solid state, the continuous filaments may be crimped or texturized and cut into a desirable fiber length, thereby producing staple fiber. The length of the staple fibers generally ranges from about 25 to about 50 millimeters, although the fibers can be longer or shorter as desired. See, for example, U.S. Pat. No. 4,789,592 to Taniguchi et al. and U.S. Pat. No. 5,336,552 to Strack et al.

The use of poly(lactic) acid in composite fibers is especially advantageous. Poly(lactic) acid develops tensile properties which are comparable or improved in comparison to the polyester and polyamide polymers traditionally employed in the core of bicomponent binder fibers.

The multicomponent fibers of the invention can be staple fibers, continuous filaments, or meltblown fibers. In general, staple, multi-filament, and spunbond fibers formed in accordance with the present invention can have a fineness of about 0.5 to about 100 denier. Meltblown filaments can have a fineness of about 0.001 to about 10.0 denier. Monofilament fibers can have a fineness of about 50 to about 10,000 denier.

As noted above, the multicomponent fibers can be incorporated into a fabric. Fibers other than the multicomponent fibers of the invention may be present as well, including any of the various synthetic and/or natural fibers known in the art. Exemplary synthetic fibers include polyolefin, polyester, polyamide, acrylic, rayon, cellulose acetate, thermoplastic multicomponent fibers (such as conventional sheath/core fibers, for example polyethylene sheath/polyester core fibers) and the like and mixtures thereof. Exemplary natural fibers include wool, cotton, wood pulp fibers and the like and mixtures thereof.

In a preferred embodiment, the multicomponent fiber of the instant invention is incorporated into a nonwoven fabric. Staple fibers of the present invention may be formed into nonwoven webs by any means known in the art, including dry laid processes, such as carding or airlaying, as well as wet laid processes. Wet laid webs are of particular interest in the present invention, and such a process is described in U.S. Pat. Nos. 5,167,765 and 5,456,982, both hereby incorporated by reference. In addition, continuous filament may be spun directly into nonwoven webs by a spunbonding process.

Alternatively, the multicomponent fibers of the invention may be incorporated, alone or in conjunction with other fibers, into a meltblown nonwoven fabric. The technique of meltblowing is known in the art and is discussed in various patents, e.g., Buntin et al., U.S. Pat. No. 3,987,185; Buntin, U.S. Pat. No. 3,972,759; and McAmish et al., U.S. Pat. No. 4,622,259.

The nonwoven webs thus formed are typically subsequently thermally bonded to transform them into nonwoven fabrics, using any thermal bonding technique known in the art.

Nonwoven fabrics which include the multicomponent fibers of the invention as a component are particularly suited for use in disposable products. Specific examples include without limitation disposable diapers, adult incontinent products, sanitary napkins, tampons, wipes, bibs, wound dressings, and surgical capes or drapes.

The nonwoven fabrics of the invention are particularly advantageous as components of a disposable diaper. Disposable diapers typically include a liquid-permeable topsheet, a backsheet attached to the liquid-permeable topsheet, and an absorbent structure positioned between the liquid-permeable topsheet and the backsheet. The nonwoven fabrics of the invention may be incorporated into any of the components which make up the disposable absorbent product, but are preferably included in the absorbent structure. Such absorbent structures are typically multilayered, comprising at least one acquisition/distribution layer and at least one storage layer. The nonwoven fabrics of the invention are particularly useful as a component of the storage layer. Exemplary disposable absorbent products are generally described in U.S. Pat. No. 4,710,187; U.S. Pat. No. 4,762,521; U.S. Pat. No. 4,770,656; and U.S. Pat. No. 4,798,603.

The fabrics of the invention can also be used as a layer in composite fabric laminate. By combining two or more nonwoven fabrics of different types, nonwoven fabric laminates have been developed for a variety of specific end use applications. Specific examples of such fabrics are described in U.S. Pat. Nos. 3,676,242; 3,795,771; 4,041,203; 4,766,029 and 4,863,785.

In an alternative embodiment, the concept of delaying the onset of polymer degradation by encapsulating the biodegradable polymer in conventional synthetic resin may be extended to other extruded articles, such as films or pultruded goods. For example, a film layer formed of a biodegradable polymer can be sandwiched between two layers of non-biodegradable polymer. The biodegradable film core typically has a melting temperature that is at least about 10° C. greater than the melting temperature exhibited by the outer layers, congruent with the other embodiments of this invention. Similarly, a pultruded article can be prepared by sandwiching a higher melt temperature biodegradable core component between two outer layers comprised of one or more non-biodegradable synthetic polymers.

The present invention will be further illustrated by the following non-limiting example.

EXAMPLE 1

Continuous multi-filament melt spun fiber is produced using a bicomponent extrusion system.

The sheath component of the bicomponent fiber consists of a high density polyethylene. The core component consists of poly(lactic) acid. The weight ratio of polyethylene to polylactic acid in the bicomponent fibers is 50/50. The sheath polymer employed is a 30 melt index high density polyethylene, commercially available as Plexar 213 from Equistar Chemical. The PLA is Heplon from Chronopol.

The two components are subjected to sheath-and-core type conventional bicomponent melt spinning.

The filaments are subsequently drawn, thereby yielding a 3 denier multifilament fiber.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A multicomponent fiber having an exposed surface and capable of controlled biodegradation comprising:
    a first component comprising a thermobondable non-biodegradable synthetic polymer forming the entire exposed surface of the multicomponent fiber; and
    a second component comprising a biodegradable polymer.

2. The fiber of claim 1, wherein said non-biodegradable synthetic polymer is selected from the group consisting of polyolefins, polyurethanes, polystyrene, acetal resins, ethylene vinyl alcohol, polyester copolymers, polyamide copolymers and blends and copolymers thereof.

3. The fiber of claim 2, wherein said polyolefin is selected from the group consisting of polyethylene, polypropylene, poly(1-butene) and blends and copolymers thereof.

4. The fiber of claim 1, wherein said non-biodegradable synthetic polymer is polyethylene.

5. The fiber of claim 1, wherein said biodegradable polymer is selected from the group consisting of polyvinyl alcohol, hydrolyzable aliphatic polyesters, hydrolyzable aliphatic polyurethanes, cis-polyisoprene, cis-polybutadiene, poly(caprolactone), poly(lactic acid), and copolymers and blends thereof.

6. The fiber of claim 5, wherein said biodegradable polymer is poly(lactic acid).

7. The fiber of claim 1, wherein said biodegradable polymer has a melting temperature of at least about 10° C. higher than the melting temperature of said non-biodegradable polymer.

8. The fiber of claim 1, wherein said fiber is selected from the group consisting of sheath/core fibers and islands in the sea fibers.

9. The fiber of claim 1, wherein said fiber has a circular cross-section.

10. The fiber of claim 1, wherein said fiber has a multi-lobal configuration.

11. The fiber of claim 1, wherein said fiber is selected from the group consisting of continuous filaments, staple fibers, and meltblown fibers.

12. A sheath/core bicomponent fiber, comprising:
    a sheath component comprising a non-biodegradable polymer having a melting temperature; and
    a core component having a melting temperature that is at least about 10° C. greater than the melting temperature of said first component, said second component comprising poly(lactic acid).

13. A process for making a multicomponent fiber capable of controlled biodegradation, comprising extruding a first polymeric component comprising a non-biodegradable synthetic polymer and a second polymeric component comprising a biodegradable polymer to produce a plurality of multicomponent fibers, each having an exposed surface, in which said non-biodegradable polymer forms the entire exposed surface thereof.

14. A fabric comprising a plurality of multicomponent fibers capable of controlled biodegradation, said multicomponent fibers having an exposed surface and comprising:
    a first component comprising a non-biodegradable synthetic polymer, wherein said first component forms the entire exposed surface of the multicomponent fiber; and
    a second component comprising a biodegradable polymer.

15. The fabric of claim 14, wherein said non-biodegradable synthetic polymer is selected from the group consisting of polyolefins, polyurethanes, polystyrene, acetal resins, ethylene vinyl alcohol, polyester copolymers, polyamide copolymers, and blends and copolymers thereof.

16. The fabric of claim 15, wherein said polyolefin is selected from the group consisting of polyethylene, polypropylene, poly(1-butene) and blends and copolymers thereof.

17. The fabric of claim 16, wherein said non-biodegradable synthetic polymer is polyethylene.

18. The fabric of claim 14, wherein said biodegradable polymer is selected from the group consisting of polyvinyl alcohol, hydrolyzable aliphatic polyesters, hydrolyzable aliphatic polyurethanes, cis-polyisoprene, cis-polybutadiene, poly(caprolactone), poly(lactic acid) and copolymers and blends thereof.

19. The fabric of claim 18, wherein said biodegradable polymer is poly(lactic acid).

20. The fabric of claim 14, wherein said fiber is selected from the group consisting of sheath/core fibers and islands in the sea fibers.

21. The fabric of claim 14, wherein said fabric is selected from the group consisting of nonwoven fabric, woven fabrics, and knit fabrics.

22. The fabric of claim 14, wherein said fabric further comprises fibers selected from the group consisting of thermoplastic fibers and natural fibers.

23. The fabric of claim 22, wherein said thermoplastic fibers are selected from the group consisting of polyolefin fibers, polyester fibers, polyamide fibers, thermoplastic multicomponent fibers, and blends thereof.

24. The fabric of claim 22, wherein said natural fibers are selected from the group consisting of wool, cotton, wood pulp and mixtures thereof.

25. An absorbent disposable article comprising at least one layer formed of a plurality of multicomponent fibers capable of controlled biodegradation, said multicomponent fibers having an exposed surface and comprising a first component comprising a non-biodegradable polymer forming the entire exposed surface of the multicomponent fiber; and a second component comprising a biodegradable polymer.

26. The disposable absorbent article of claim 25, wherein said article is a diaper.

27. The disposable absorbent article of claim 26, wherein said article is a diaper comprising:

a liquid pervious topsheet;

a liquid impervious backsheet joined to said topsheet; and a multiple layer absorbent core positioned between said topsheet and said backsheet, wherein said multiple layer absorbent core comprises said multicomponent fiber.

28. A process for controlling the biodegradation of fabrics having a biodegradable component, said process comprising heat treating a fabric comprising a plurality of multicomponent fibers having an exposed surface, said multicomponent fibers comprising a first component comprising a non-biodegradable polymer forming the entire exposed surface of the multicomponent fiber; and a second compartment comprising a biodegradable polymer at a temperature sufficient to melt at least a portion of said first component to expose said second biodegradable component to conditions sufficient to initiate the subsequent degradation of said biodegradable component.

29. A multicomponent fiber having an exposed surface comprising:

a first component comprising a thermobondable non-biodegradable synthetic polymer forming at least a portion of the exposed surface of the multicomponent fiber; and a second component comprising a biodegradable polymer, said fiber having been heat treated at a temperature sufficient to melt at least a portion of said first component to expose said second biodegradable component to conditions sufficient to initiate the subsequent degradation of said biodegradable component.

30. A fabric comprising a plurality of multicomponent fibers, the multicomponent fibers having an exposed surface and comprising:

a first component comprising a non-biodegradable synthetic polymer, wherein said first component forms at least a portion of the exposed surface of a multicomponent fiber; and a second component comprising a biodegradable polymer, said fabric having been heat-treated at a temperature sufficient to melt at least a portion of said first component to expose said second biodegradable component to conditions sufficient to initiate the subsequent degradation of said biodegradable component.

31. A sheath/core fiber having an exposed surface and capable of controlled biodegradation comprising:

a sheath component comprising a thermobondable non-biodegradable synthetic polymer forming the entire exposed surface of the sheath/core fiber; and a core component comprising a biodegradable polymer.

32. The sheath/core fiber of claim 31, wherein said non-biodegradable synthetic polymer is selected from the group consisting of polyolefins, polyurethanes, polystyrene, acetal resins, ethylene vinyl alcohol, polyester copolymers, polyamide copolymers and blends and copolymers thereof.

33. The sheath/core fiber of claim 32, wherein said polyolefin is selected from the group consisting of polyethylene, polypropylene, poly(1-butene) and blends and copolymers thereof.

34. The sheath/core fiber of claim 33, wherein said polyolefin is polyethylene.

35. The sheath/core fiber of claim 31, wherein said biodegradable polymer is selected from the group consisting of polyvinyl alcohol, hydrolyzable aliphatic polyesters, hydrolyzable aliphatic polyurethanes, cis-polyisoprene, cis-polybutadiene, poly(caprolactone), poly(lactic acid), and copolymers and blends thereof.

36. The sheath/core fiber of claim 35, wherein said biodegradable polymer is poly(lactic acid).

37. An islands in the sea fiber having an exposed surface and capable of controlled biodegradation comprising:

a sea component comprising a thermobondable non-biodegradable synthetic polymer forming the entire exposed surface of the islands in the sea fiber; and a plurality of island components located within said sea component and comprising a biodegradable polymer.

38. The islands in the sea fiber of claim 37, wherein said non-biodegradable synthetic polymer is selected from the group consisting of polyolefins, polyurethanes, polystyrene, acetal resins, ethylene vinyl alcohol, polyester copolymers, polyamide copolymers and blends and copolymers thereof.

39. The islands in the sea fiber of claim 38, wherein said polyolefin is selected from the group consisting of polyethylene, polypropylene, poly(1-butene) and blends and copolymers thereof.

40. The islands in the sea fiber of claim 39, wherein said polyolefin is polyethylene.

41. The islands in the sea fiber of claim 37, wherein said biodegradable polymer is selected from the group consisting of polyvinyl alcohol, hydrolyzable aliphatic polyesters, hydrolyzable aliphatic polyurethanes, cis-polyisoprene, cis-polybutadiene, poly(caprolactone), poly(lactic acid), and copolymers and blends thereof.

42. The islands in the sea fiber of claim 41, wherein said biodegradable polymer is poly(lactic acid).

43. A fabric comprising a plurality of sheath/core fibers having an exposed surface and capable of controlled biodegradation, said sheath/core fibers comprising:

a sheath component comprising a non-biodegradable synthetic polymer, wherein said sheath component forms the entire exposed surface of the sheath/core fiber; and a core component comprising a biodegradable polymer.

44. A fabric comprising a plurality of islands in the sea fibers having an exposed surface and capable of controlled biodegradation, said islands in the sea fibers comprising:

a sea component comprising a non-biodegradable synthetic polymer, wherein said sea component forms the entire exposed surface of the multicomponent fiber; and a plurality of island components located within said sea component and comprising a biodegradable polymer.

* * * * *

UNITED STATES PATENT AND TRADEMARK OFFICE
CERTIFICATE OF CORRECTION

PATENT NO.    : 6,441,267 B1
DATED         : August 27, 2002
INVENTOR(S)   : Dugan It is certified that error appears in the above-identified patent and that said Letters Patent is hereby corrected as shown below:

Column 11,
Lines 35-36, "at least a portion of the" should read -- the entire --;
Lines 48-49, "at least a portion of the" should read -- the entire --.

Signed and Sealed this

Sixth Day of May, 2003

JAMES E. ROGAN
*Director of the United States Patent and Trademark Office*